US00PP34000P2

(12) United States Plant Patent
Van Swieten

(10) Patent No.: US PP34,000 P2
(45) Date of Patent: Mar. 8, 2022

(54) ***PHALAENOPSIS* ORCHID PLANT NAMED 'PHA1710186'**

(50) Latin Name: ***Phalaenopsis* hybrid**
Varietal Denomination: PHA1710186

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,580

(22) Filed: Aug. 25, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

CPVO hit on *Phalaenopsis* plant named, 'PHA1710186', having UPOV application No. QZ PBR 2020/2295, filed Sep. 22, 2020.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHA1710186', particularly characterized by having white flowers with a pure white and extra-large lip, flowers that are flat in lateral view, rectangular apical lobes, and is propagated by meristem tissue culture, is disclosed.

3 Drawing Sheets

Genus and species: *Phalaenopsis* hybrid.
Variety denomination: 'PHA1710186'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1710186'.

The new *Phalaenopsis* plant is a product of a planned breeding program conducted by the inventor in Bleiswijk, the Netherlands. The objective of this breeding program was to create a new *Phalaenopsis* plant with numerous attractive white flowers with a white and extra-large lip, suitable for potted plant production.

The new *Phalaenopsis* plant 'PHA1710186' is a result of cross-pollination made by the inventor in July 2013 in Bleiswijk, the Netherlands, of the proprietary female, or seed parent, *Phalaenopsis* hybrid '44451-06' (unpatented) with the proprietary male, or pollen parent, *Phalaenopsis* hybrid '01-1988' (unpatented).

The new *Phalaenopsis* was selected by the inventor as a single plant within the progeny of the stated cross-pollination in a controlled greenhouse in Bleiswijk, the Netherlands, in June 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020

(Application no. 2020/2295), by Applicant who obtained the subject matter disclosed directly from the inventor. 'PHA1710186' has not been made publicly available or sold anywhere in the world prior to the effective filing date of this application with the exception of sales or disclosures made one year or less before the effective filing date of this claimed invention by Applicant who obtained 'PHA1710186' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1710186' as a new and distinct variety of *Phalaenopsis* plant:

1) White flowers with a white and extra-large lip;
2) Lip is pure white;
3) Flower shape in lateral view is flat; and
4) Shape of apical lobe is rectangular.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in July 2021. Colors in the photographs may differ from the color values cited in the detailed botanical description, which accurately describe the actual colors of the new variety.

DESCRIPTION OF THE NEW VARIETY

Figure 1:
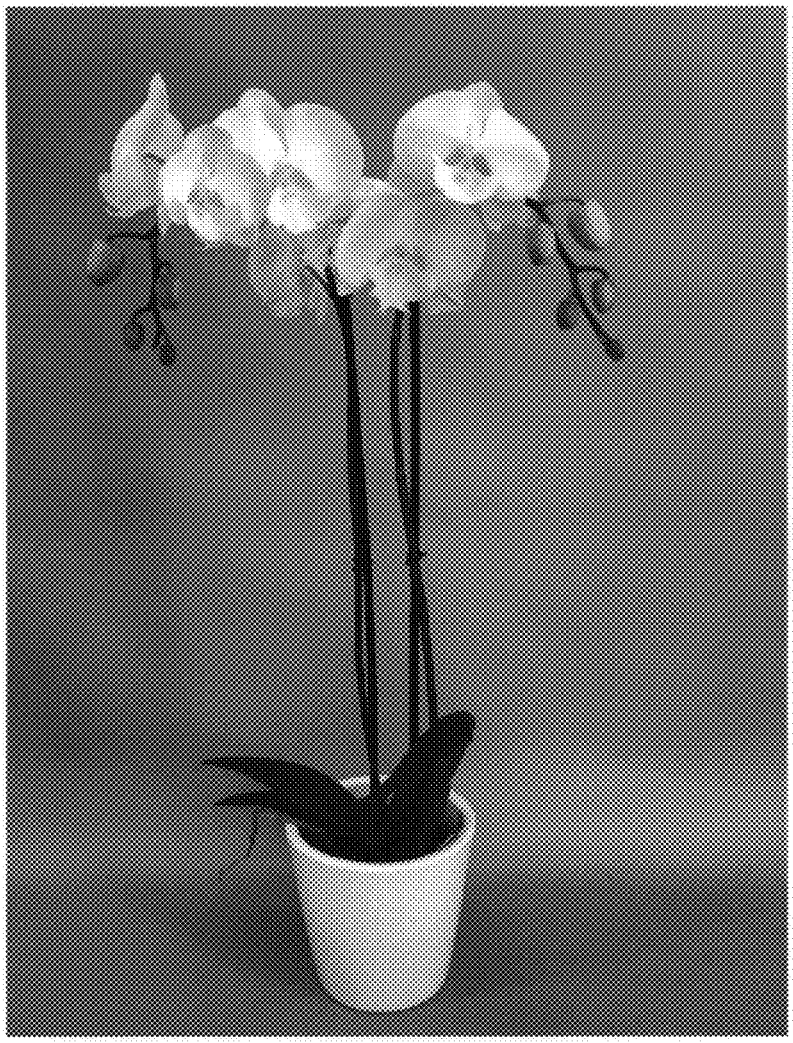
FIG. 1 shows the overall plant habit, including blooms, buds, and foliage of 'PHA1710186'.
Figure 2:
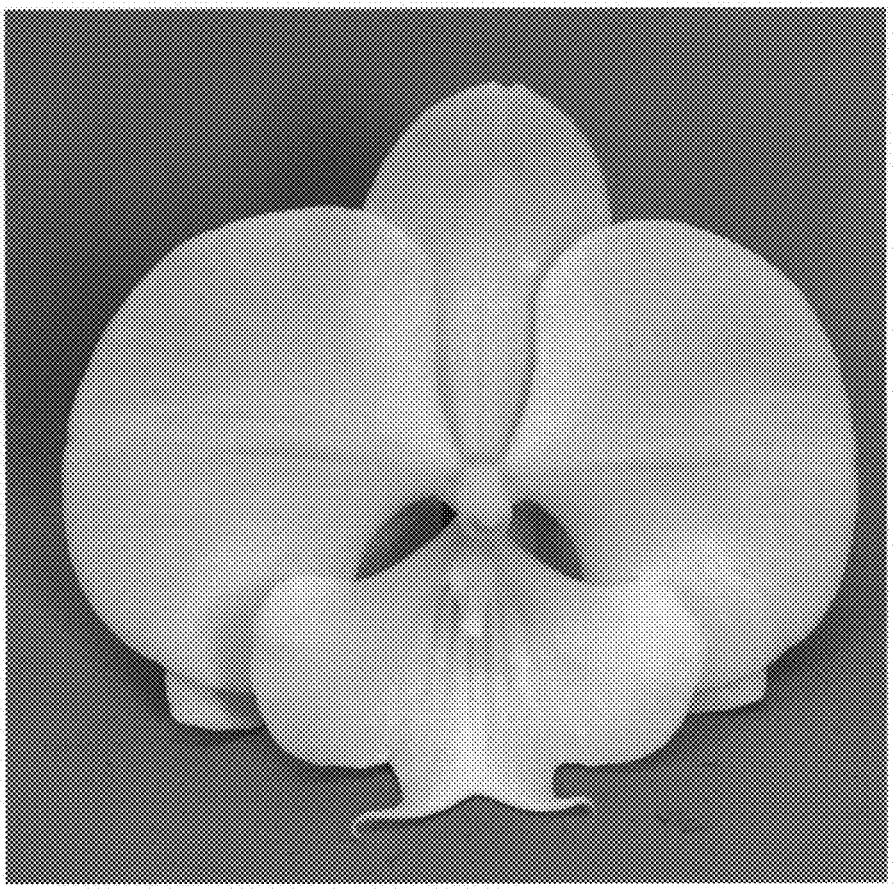
FIG. 2 shows a close-up of a flower of 'PHA1710186'.
Figure 3:
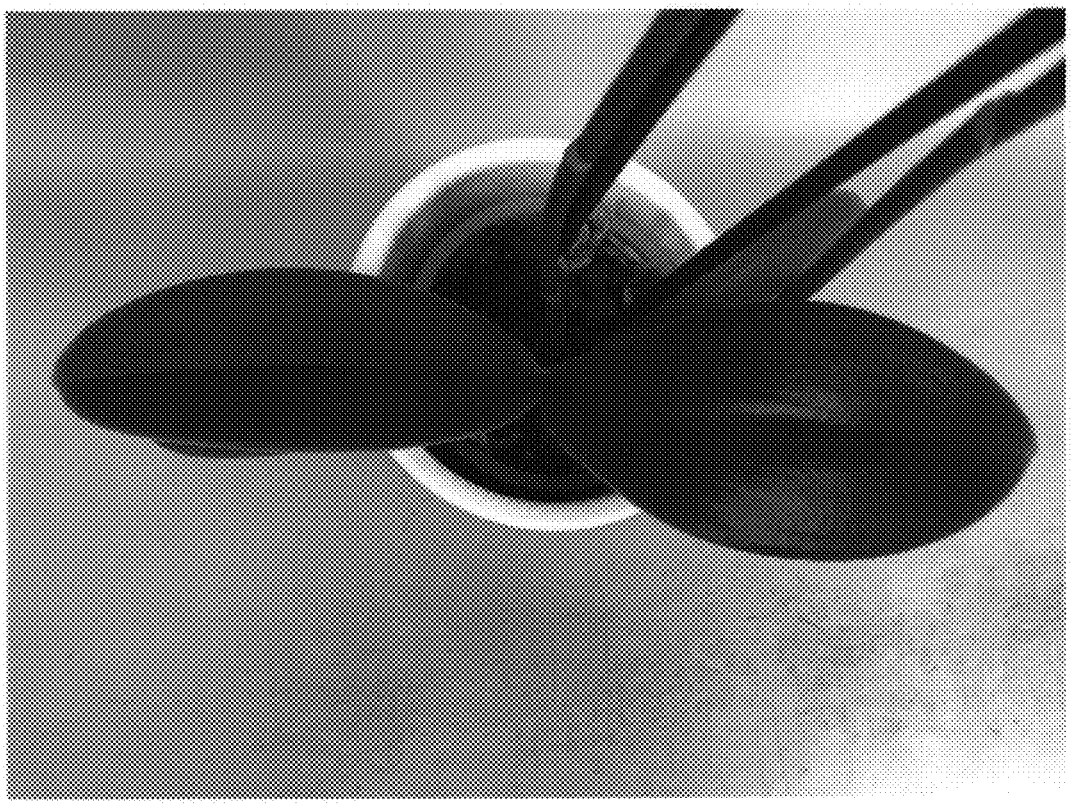
FIG. 3 shows an overhead view of the leaves of 'PHA1710186'.

The following detailed description sets forth the distinctive characteristics of 'PHA1710186'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1710186'.

Parentage:

*Female parent*.—*Phalaenopsis* cultivar '44451-06' (unpatented).

*Male parent*.—*Phalaenopsis* cultivar '01-1988' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 144C) and small yellowish-green (RHS N144A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height (from soil level to top of inflorescence)*.—Approximately 60.0 cm to 70.0 cm.

*Width (measured from leaf tips)*.—About 28.0 cm to 31.0 cm.

*Vigor*.—Moderate.

Leaves:

*Mature leaves*.—Quantity per plant: 6 to 7 leaves are produced before flowering. Length (fully expanded): 15.0 cm to 17.0 cm. Width: 6.5 cm to 7.5 cm. Shape: Oblong. Base shape: Moderately elongated. Apex: Acute unequal. Leaf blade angle with the petiole (measured from the horizontal position): Between 15 degrees and 30 degrees. Leaf margin: Entire. Color: Upper surface: RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146A.

Peduncle:

*Quantity per plant*.—1 to 2.

*Number of flowers per peduncle*.—9 to 12.

*Length*.—60.0 cm to 70.0 cm.

*Diameter*.—5.0 mm to 6.0 mm.

*Strength*.—Strong.

*Aspect*.—Upright to slightly pendent.

*Texture*.—Smooth.

*Color*.—Yellow-green (RHS 146A and RHS 146D) with a touch of reddish-brown (RHS 200B).

*Internode length*.—3.5 cm to 4.5 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 250.0 mm to 300.0 mm.

*Flowering time*.—First flowers can be expected 10 to 11 months after planting in a 12-cm pot.

*Flower*.—Height: 85.0 mm to 90.0 mm. Diameter: 93.0 mm to 98.0 mm. Depth of lip: About 19.0 mm.

*Flower shape*.—Flat.

*Flower longevity*.—On the plant: 13 to 15 weeks.

*Fragrance*.—Absent.

*Flower bud*.—Average size: Medium to large. Length: 20.0 mm to 22.0 mm. Width: 10.0 mm to 12.0 mm. Shape: Egg shaped. Color: Light yellow-green (a color in between RHS N144D and RHS 145C) with a touch of light reddish-purple (RHS N78D).

*Petals*.—Arrangement: Open/free. Shape: Semi-circular. Apex: Rounded slightly asymmetric. Margin: Weakly undulated. Length (from base to tip): 44.0 mm to 46.0 mm. Width: 58.0 mm to 60.0 mm. Position of the broadest part of the petal: At the base. Color (when fully opened): Upper surface: Basic color: White (RHS NN155C). Over color: Absent. Lower surface: Basic color: White (RHS NN155C). Over color: Very light purple midvein (RHS 76B). Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 47.0 mm to 49.0 mm. Width: 32.0 mm to 34.0 mm. Color (when fully opened): Upper surface: Basic color: White (RHS NN155C). Over color: Absent. Lower surface: Basic color: White (RHS NN155C). Over color: Very light purple (RHS 76B) and light yellow-green (RHS 145C). Number of spots and stripes on the dorsal sepals (upper surface): None. Color of spots and stripes on the dorsal sepals (upper surface): Not applicable. Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 48.0 mm to 50.0 mm. Width: 26.0 mm to 28.0 mm. Color (when fully opened): Upper surface: Basic color: White (RHS NN155C). Over color: Absent. Lower surface: Basic color: White (RHS NN155C). Over color: Touch of light yellow-green (RHS 145C) and very light purple (RHS 76B); light purple midvein (RHS 75A) toward apex. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Overall shape: 3-lobed with callus at central junction of the lateral lobes and base of apical lobe. The apical lobe is terminated by 2 whiskers. Lateral lobes and apical lobe are connected.

*Lateral lobe*.—Margin: Moderately undulated. Length: 21.0 mm to 23.0 mm. Width: 21.0 mm to 23.0 mm. Color: Upper surface: White (RHS NN155C). Lower surface: White (RHS NN155C) with a touch of very light purple (RHS 76C). Number of spots and stripes on the lateral lobe (upper surface): None. Color of spots and stripes on the lateral lobe (upper surface): Not applicable. Density of netting of the lateral lobe (upper surface): None. Color of the netting (upper surface): Not applicable.

*Apical lobe*.—Shape: Rectangular. Margin: Entire. Length: 4.0 mm to 6.0 mm. Width: 17.0 mm to 19.0 mm. Color: Upper surface: White (RHS NN155C). Lower surface: White (RHS NN155C). Number of spots and stripes on the apical lobe (upper surface): None. Color of spots and stripes on the apical lobe (upper surface): Not applicable. Density of netting of the apical lobe (upper surface): None. Color of the netting (upper surface): Not applicable. Whiskers: Present. Length of whiskers: 14.0 mm to 16.0 mm. Color of whiskers: White (RHS NN155C). Pubescence on the lip: Absent.

*Callus*.—Average size: Small to medium. Height: 2.0 mm to 3.0 mm. Length: 6.0 mm to 7.0 mm. Width: 2.0 mm to 3.0 mm. Color: White (RHS NN155C) with yellow-green margins (RHS 150C).

Reproductive organs:

*Column*.—Length: 10.0 mm to 11.0 mm. Diameter: 5.0 mm to 6.0 mm. Color: White (RHS NN155C).

*Pollinia*.—Quantity: 2. Diameter: 0.9 mm to 1.1 mm. Color: Orange (RHS N25C).

*Ovary*.—Length: 12.0 mm to 14.0 mm. Diameter: 2.2 mm to 2.5 mm.

*Pedicel*.—Length: 40.0 mm to 42.0 mm. Diameter: 2.6 mm to 3.0 mm. Color: Yellow-green (RHS 146D) with a touch of reddish-brown (a color in between RHS 200B and RHS 200C) at the base; lighter yellow-green (RHS 145B) and very light purple (RHS 76B) toward flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1710186' differs from the female parent plant '44451-06' (unpatented) in that 'PHA1710186' has rectangular apical lobes, whereas '44451-06' has trapezoid apical lobes. Additionally, 'PHA1710186' has smaller flowers than '44451-06'.

'PHA1710186' differs from the male parent plant '01-1988' (unpatented) in that 'PHA1710186' has rectangular apical lobes, white whiskers, and an extra-large lip type, whereas '01-1988' has triangular apical lobes, yellow whiskers, and a normal lip type. Additionally, 'PHA1710186' has smaller flowers than '01-1988'.

'PHA1710186' is most similar to the commercial *Phalaenopsis* plants named 'PHALGASEOT' (U.S. Plant Pat. No. 31,212) and 'PHA1437158' (unpatented). 'PHA1710186' differs from the commercial variety 'PHALGASEOT' in that 'PHA1710186' has white calluses with yellow-green margins, whereas 'PHALGASEOT' has light yellow-green calluses with very small dots. Additionally, 'PHA1710186' has larger flowers, wider petals, longer whiskers, and shorter internodes than 'PHALGASEOT'.

'PHA1710186' differs from the commercial variety 'PHA1437158' in that 'PHA1710186' has emarginated dorsal sepal apexes and calluses that are white with yellow-green margins, whereas 'PHA1437158' has obtuse dorsal sepal apexes and calluses that are light yellow-green at the base, yellow-green on the sides, and dotted. Additionally, 'PHA1710186' has smaller flowers, narrower petals, and shorter leaves than 'PHA1437158'.

I claim:

1. A new and distinct variety of *Phalaenopsis* plant named 'PHA1710186', substantially as described and illustrated herein.

* * * * *